(12) United States Patent
Christa et al.

(10) Patent No.: US 8,293,876 B2
(45) Date of Patent: Oct. 23, 2012

(54) METHOD OF PURIFICATION OF HYDROPHOBIC PROTEINS

(75) Inventors: Tauer Christa, Vienna (AT); Mitterer Artur, Orth/Donau (AT)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 1204 days.

(21) Appl. No.: 12/033,316

(22) Filed: Feb. 19, 2008

(65) Prior Publication Data
US 2008/0249014 A1    Oct. 9, 2008

Related U.S. Application Data

(60) Provisional application No. 60/902,803, filed on Feb. 22, 2007.

(51) Int. Cl.
*C07K 14/00* (2006.01)
*G01N 30/00* (2006.01)

(52) U.S. Cl. .................. 530/417; 435/70.1

(58) Field of Classification Search .......... None
See application file for complete search history.

(56) References Cited

U.S. PATENT DOCUMENTS

| | | | |
|---|---|---|---|
| 5,543,399 A * | 8/1996 | Riordan et al. | 514/1.5 |
| 5,861,295 A | 1/1999 | Goldstein et al. | |
| 6,602,697 B1 | 8/2003 | Cook | |
| 2004/0072314 A1 * | 4/2004 | Champluvier et al. | 435/183 |

FOREIGN PATENT DOCUMENTS

| | | |
|---|---|---|
| EP | 0 336 736 | 10/1989 |
| EP | 0 522 560 | 1/1993 |
| WO | WO 97/47197 | 12/1997 |

OTHER PUBLICATIONS

Rucevic et al., "Use of short monolithic columns for isolation of low abundance membrane proteins", Journal of Chromatography A, 1123: 199-204 (2006).*

Wenk et al., "Novel, rapid purification of the membrane protein photosystem I by high-performance liquid chromatography on porous materials", Journal of Chromatography B, 737: 131-142 (2000).*

Josic and Zeilinger, Methods in Enzymology, vol. 271, [5] Membrane Proteins, pp. 113-134 (1996).*

Pharmacia Fine Chemicals, Ion Exchange Chromatography principles and methods, pp. 4-39 (1980).*

Haupl et al., "Activation of Monocytes by Theree OspA Vaccine Candidates: Lipoprotein OspA is a Potent Simulator of Monokines," 1997, FEMS Immunology and Medical Microbiology, vol. 19, pp. 15-23.

International Search Report dated May 28, 2008, issued in related International Patent Application No. PCT/EP2008/001284, filed Feb. 19, 2008.

* cited by examiner

*Primary Examiner* — Anand Desai
(74) *Attorney, Agent, or Firm* — Kilpatrick Townsend & Stockton LLP

(57) ABSTRACT

The present invention relates to a method for obtaining highly purified hydrophobic proteins from cells by extraction using a buffer containing a detergent and removal of said detergent by hydroxyapatite (HA) column chromatography.

40 Claims, 10 Drawing Sheets

11 MR
12 MF
13 MDR1
14 MDF1
15 MDR2
16 MDF2
17 1 x 800 bar pellet
18 MR pellet
19 MDR1 pellet
20 MDR2 pellet

METHOD OF PURIFICATION OF HYDROPHOBIC PROTEINS

CROSS-REFERENCES TO RELATED APPLICATIONS

This application claims priority to U.S. Provisional Patent Application No. 60/902,803, filed on Feb. 22, 2007, which is herein incorporated by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The present invention relates to a method for obtaining highly purified hydrophobic proteins from cells by extraction using a buffer containing a detergent and removal of said detergent by hydroxyapatite (HA) column chromatography.

BACKGROUND OF THE INVENTION

A promising concept for extraction and solubilization of membrane proteins, particularly hydrophobic proteins, is the use of a detergent. Detergents are amphipathic molecules, which contain polar and non-polar chemical groups. Consequently, they exhibit unique properties in water. They are soluble in water and can solubilize hydrophobic proteins by interacting with hydrophobic domains (for example transmembrane regions). Numerous detergents are known to the public domain but in principle they can be divided into non-ionic, ionic and zwitterionic detergents. The solubilizing potency of detergents varies depending on the hydrophilic/lipophilic balance (HLB) of the amphiphilic groups in the molecule. Detergents with high solubilization power (like Sodium Dodecyl Sulfate—SDS) have also denaturing effects on the structure of the proteins to be solubilized. The selection of the appropriate detergent for the intended use is therefore dependent on the properties of the target protein and the technical conditions of the process (see, e.g., L. M. Hjelmeland and A. Chrambach, "Solubilization of Functional Membrane Proteins", *Meth. Enzymol.*, 1984, Vol. 104, Part C, pages 305-328).

One of the major disadvantages of using detergents for solubilizing biomolecules such as proteins is the contamination of the desired biomolecule with the detergent itself. Complete removal of the detergent is generally time-consuming and tedious, or even impossible in some cases. Further, by requiring high number of post-extraction purification steps the resulting overall yield of the desired product can decrease to an uneconomical degree.

Further, the most common method known in the art for cell debris separation is centrifugation. However, centrifugation, especially in view of an industrial large production scale process, shows a variety of drawbacks, such as high cost of industrial scale centrifuges and low efficacy in case of fine particles.

Thus, a strong need exists for a method useable in obtaining a highly purified hydrophobic protein from cells which overcome the above-mentioned disadvantages.

Therefore, it is an object of the present invention to provide a new method for obtaining highly purified proteins from cells, such as membrane proteins, particularly hydrophobic proteins.

BRIEF SUMMARY OF THE INVENTION

The present invention relates to a method for obtaining a highly purified hydrophobic protein from cells which uses a detergent to solubilize said protein and a hydroxyapatite column chromatography step for subsequent detergent removal.

The method according to the present invention is highly effective in purifying lipidated proteins such as proteins which naturally occur as membrane-bound proteins of a species of a prokaryote or eukaryote. By using a detergent to solubilize the desired hydrophobic protein e.g. from a host cell the target protein is efficiently isolated. The method of the present invention can, for example, be used to purify recombinant Synthetic Lyme Antigens ("rSLA's"), which comprise domains of outer surface proteins (OspA) proteins from two separate genotypes of *Borrelia* sp.

The present invention further relates to a pharmaceutical composition which comprises a hydrophobic protein, such as a lipidated protein, obtained from the method according to the present invention.

BRIEF DESCRIPTION OF THE DRAWINGS

FIG. 7).

DETAILED DESCRIPTION OF THE INVENTION

Figure 1:
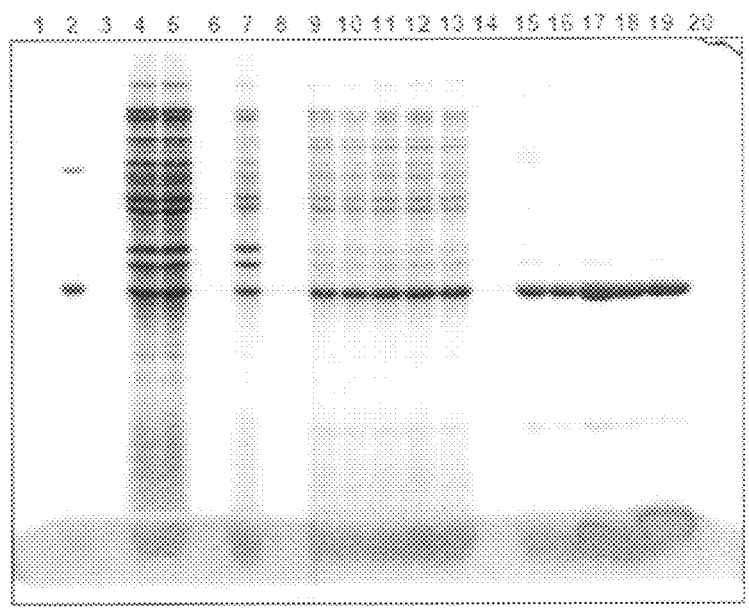
FIG. 1 shows a photograph of the Coomassie gel, displaying bacterial cell extracts, in which different TRITON™ X100 concentrations were tested. Purified chimeric rSLA of the serotype 5/3 was used as a reference (lane 2). Increasing TRITON™ X100 concentrations (0.5% to 3.0% in half percent increment) were used for extractions (lanes 9-13). The SDS PAGE showed a dependence of extraction efficiency corresponding to increasing TRITON™ X100 concentrations (lane 9-13). After DE 53-anion exchange chromatography, the bulk of *E. coli* proteins in the supernatant ("SN DE53") were bound onto the resin whereas rSLA did not bind (lanes 15-19). Best yields in combination with acceptable purity were observed with 1.5% TRITON™ X100 (lane 17).

One aspect of the present invention relates to a method for obtaining a highly purified hydrophobic protein from cells according to the present invention, comprising the steps of:
(i) subjecting a cell homogenate to microfiltration;
(ii) extracting the retentate obtained from said microfiltration by microdiafiltration using a buffer-solution containing at least one detergent; and
(iii) subjecting the filtrate obtained from said microdiafiltration to hydroxyapatite (HA) column chromatography.

According to the method of the present invention in step (i) the cell homogenate is subjected to microfiltration to remove soluble impurities (wash step). Step (iii) of the above-defined method according to the present invention may contain, beside the HA column chromatography, one or more steps of column chromatography to remove the detergent and further impurities.

Herein, the expression "highly purified" means, for example, a purity of said hydrophobic protein after hydroxyapatite column chromatography of higher than 99%, wherein after hydroxyapatite column chromatography the content of impurities is, for example, below 1%, preferably below 0.5%.

The term "impurities" as used herein, includes any impurity originating from the production of the hydrophobic protein and may include for example host cell proteins, host cell nucleic acids, process related impurities such as buffers and salts, impurities originating from the cell culture medium and product related impurities such as multimers or fragments. Impurities exclude desired final composition components, for example, end buffer formulation components, or additives such as adjuvants, excipients, or preservatives which may be added to the purified protein for a final therapeutic composition.

According to the present invention, the term "hydrophobic protein" does not underlie a specific restriction and includes any hydrophobic protein which can be purified from cells by using the method as defined above. Further, said term does not relate to a specific value or range of hydrophobicity, but means any hydrophobicity which renders the target protein insoluble in aqueous solutions through the association with cellular structures or self association and allows for the purification of said protein by the above-defined method. Said term "hydrophobic protein" further includes the protein itself, for example a membrane protein, as well as any biologically active derivative thereof. According to the present invention, the term "biologically active derivative" includes any derivative of a protein, protein complex or polypeptide having substantially the same functional and/or biological properties of said hydrophobic protein such as binding properties, and/or the same structural basis, such as peptidic backbone. Minor deletions, additions and/or substitutions of amino acids of the polypeptide sequence of the target protein which are not altering the biological activity of said polypeptide are also included in the present application as biologically active derivatives.

According to the present invention, the hydrophobic protein purified using the methods of the invention may be a lipidated protein, such as a protein which naturally occurs as a membrane-bound protein of a species of a prokaryote or eukaryote. For example, the lipidated protein may naturally occur as a membrane-bound protein in a bacterial species. According to another example of the present invention, the hydrophobic protein to be purified is a lipoprotein from *Borrelia*.

The term "lipidated protein" used herein means any peptide or protein which is covalently or non-covalently associated with a lipid. One example of lipidated proteins is the group of outer surface proteins (Osp proteins) of *Borrelia* sp.

The method according to the present invention has been shown to be particularly useful for purifying lipidated Osp-like proteins. Osp-like proteins which may be purified by the methods of the present invention include lipidated proteins which are structurally similar to the OspA protein of *Borrelia* sp. Structural similarity may for example be determined by a protein-protein BLAST comparison of the protein sequence of the purified protein to OspA proteins, according to the methods described in: Altschul, Stephen F., Thomas L. Madden, Alejandro A. Schäf-fer, Jinghui Zhang, Zheng Zhang, Webb Miller, and David J. Lipman, "Gapped BLAST and PSI-BLAST: a new generation of protein database search programs", *Nuc. Acids Res.*, 1997, 25:3389-3402; and Schaffer, Alejandro A., L. Aravind, Thomas L. Madden, Sergei Shavirin, John L. Spouge, Yuri I. Wolf, Eugene V. Koonin, and Stephen F. Altschul, "Improving the accuracy of PSI-BLAST protein database searches with composition-based statistics and other refinements", 2001, *Nuc. Acids Res.*, 29:2994-3005. Software for performing BLAST analyses is publicly available through the National Center for Biotechnology Information website (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength (W) of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

In some embodiments, the protein purified by the methods of the invention has at least 50% identity to an OspA protein of a *Borrelia* sp. over at least 130 contiguous amino acids of the sequence. In other embodiments, the protein purified by the methods of the invention has at least 60% identity to an OspA protein of a *Borrelia* sp. over at least 130 contiguous amino acids of the sequence. In other embodiments, the protein purified by the methods of the invention has at least 70% identity to an OspA protein of a *Borrelia* sp. over at least 130 contiguous amino acids of the sequence. In other embodiments, the protein purified by the methods of the invention has at least 75% identity to an OspA protein of a *Borrelia* sp. over at least 130 contiguous amino acids of the sequence. In other embodiments, the protein purified by the methods of the invention has at least 80% identity to an OspA protein of a *Borrelia* sp. over at least 130 contiguous amino acids of the sequence. In other embodiments, the protein purified by the methods of the invention has at least 85% identity to an OspA protein of a *Borrelia* sp. over at least 130 contiguous amino acids of the sequence. In other embodiments, the protein purified by the methods of the invention has about 87% identity to an OspA protein of a *Borrelia* sp. over at least 130 contiguous amino acids of the sequence.

According to one embodiment of the present invention, the protein purified by the method of the invention has a BLAST score of least 360 when compared to an OspA protein of a *Borrelia* sp. In other embodiments, the protein purified by the method of the invention has a BLAST score of least 400 when compared to an OspA protein of a *Borrelia* sp. In other embodiments, the protein purified by the method of the invention has a BLAST score of least 440 when compared to an OspA protein of a *Borrelia* sp. In other embodiments, the protein purified by the method of the invention has a BLAST score of least 480 when compared to an OspA protein of a *Borrelia* sp. In other embodiments, the protein purified by the method of the invention has a BLAST score of least 520 when compared to an OspA protein of a *Borrelia* sp. In other embodiments, the protein purified by the method of the invention has a BLAST score of least 560 when compared to an OspA protein of a *Borrelia* sp. In other embodiments, the protein purified by the method of the invention has a BLAST score of least 580 when compared to an OspA protein of a *Borrelia* sp. In other embodiments, the protein purified by the method of the invention has a BLAST score of least 600 when compared to an OspA protein of a *Borrelia* sp. In other embodiments, the protein purified by the method of the invention has a BLAST score of least 620 when compared to an OspA protein of a *Borrelia* sp.

In the examples, the methods of the invention are used to purify recombinant Synthetic Lyme Antigens ("rSLA's"), which comprise domains of OspA proteins from two separate genotypes of *Borrelia* sp., as well as stabilizing point mutations. OspA proteins suitable for use with the present invention are well known in the art. Non-limiting exemplary OspA protein sequences suitable for use with the present invention can be derived from *Borrelia burgdorferiss* (GenBank accession no. Q45050), *Borrelia afzelii* (GenBank accession no. Q0SLZ0), and *Borrelia garinii* (GenBank accession nos. Q1HLI9, Q44959, Q44961, and Q932R4). When compared to the OspA sequences in GenBank, the rSLA's have identities to OspA sequences ranging from about 56% to about 87% over at least 130 contiguous amino acids of the sequence, and have BLAST scores ranging from about 360 to about 620 when compared to various OspA protein of a *Borrelia* sp.

The hydrophobic protein according to the present invention may be produced by any method known in the art. This may include any method known in the art (i) for the production of recombinant DNA by genetic engineering, e.g. via reverse transcription of RNA and/or amplification of DNA, (ii) the introduction of recombinant DNA into prokaryotic or eukaryotic cells by transfection, e.g. via chemically mediated transfection, electroporation or microinjection, (iii) the cultivation of said transformed cells, e.g. in a continuous or batch-wise manner, (iv) the expression of the hydrophobic protein, e.g. constitutive or upon induction, and (v) the isolation of the protein, e.g. from the culture medium or by harvesting the transformed cells, in order to obtain the hydrophobic protein. Additionally, the recombinant DNA coding for said hydrophobic protein, e.g. a plasmid, may also contain a DNA sequence encoding a selectable marker for selecting the cells which have been successfully transfected with the recombinant DNA. According to one example of the present invention, the hydrophobic protein is obtained from harvested cultured cells according to any method known in the art.

The expression "cell homogenizate" means according to the present invention any kind of cell homogenizate obtainable by any homogenization and/or cell disruption process known to the person skilled in the art. These processes for preparing a cell homogenizate according to the present invention include for example grinding, high-speed mixing, mincing, chopping, sonication, pressure changes, osmotic shock, freeze-thawing as well as addition of cell disrupting agents such as enzymes or detergents, or any combination of such processes.

The term "buffer-solution" as used in the present invention, includes any buffer usable in the purification of proteins as known to the person skilled in the art, as well as any mixture of two or more of such buffers. Examples of such buffer solutions are water, Tris-buffer, phosphate buffer, or citrate buffer. However, the buffers usable in the method of the present invention are not limited in a specific way and can further contain any substance or mixture of substances useful in the purification of a protein, such as protein stabilizers. Further, the concentrations of the respective buffers which are used in each of the steps of the method according to the present invention and are not specifically limited, i.e. said buffer concentrations may be the same or different in each of the respective steps, depending on the requirements thereof. For example, the buffer concentrations may be in the range from about 0.1 mM to about 1.0 M or in the range from about 1 mM to about 600 mM. Moreover, the pH-value of the buffers used in the method according to the present invention does not underlie a specific restriction, as long as it is in a range which allows operability of the above-defined method. According to one example of the present invention, the pH-value of the respective buffer ranges from about 3 to about 10, or from about 6 to about 8.

According to a specific example of the present invention, the buffer used in the microfiltration step (i) of the above-defined method is a Tris-buffer. In a further example of the present invention, the buffer used in the extraction step (ii) of the method as defined above is a Tris-buffer containing a detergent. According to an-other example of the method according to the present invention, the buffer used in the hydroxyapatite column chromatography step (iii) is a sodium phosphate-buffer.

The term "detergent" used according to the present invention includes any amphipathic substance or mixture of amphipathic substances and can, for example, increase the dissolution or dispersibility of a hydrophobic substance in an aqueous solution. The term detergent generally relates to an organic compound that contains both hydrophobic and hydrophilic groups. A detergent usable in the method of the present invention may for example be ionic, zwitterionic or nonionic. The detergent usable in the method of the present invention does not underlie a specific restriction, as long as it has no negative impact on the purification of said hydrophobic protein, and may further consist of a mixture comprising two or several distinct detergents.

According to one example of the present invention, in the method as defined above, the cell homogenate is washed using a suitable buffer, prior to extraction step (ii).

The term "suitable buffer" as used herein does not underlie a specific restriction and includes any buffer which allows for washing the homogenizate without dissolving the desired hydrophobic protein to an undesired extent. Examples of suitable buffers for washing the homogenate include Tris-buffer, HEPES-buffer, citrate-buffer or phosphate-buffer.

According to another example of the present invention, in the above-defined method, the filtrate obtained from said extraction step (ii) is subjected to ion exchange chromatography, prior to hydroxyapatite column chromatography step (iii).

The ion exchange chromatography material (resin) used in the method of the present invention does not underlie a specific restriction, as long as the above-defined impurities being removed to obtain a highly purified hydrophobic protein. According to the present invention, the ion exchange resin includes any material suitable for ion exchange chromatography. In a specific example of the present invention, the ion exchange resin contains positively charged groups and is therefore an anion exchange material. A preferred option is DE-53, an anion exchange resin based on cellulose material.

The buffers usable in the ion exchange chromatography step are not limited in a specific way and include any buffer known in the art usable in ion exchange chromatography. Suitable buffers consist of Tris-buffer, HEPES-buffer, citrate-buffer or phosphate-buffer or mixtures thereof.

According to the present invention, the extraction step (ii) of the above-defined method may contain additional steps, such as concentrating steps, washing steps etc., which may be in any order and/or any combination. According to a specific example of the present invention, the extraction step (ii) of the above-defined method comprises the steps of (a) washing the biomass and reclaiming by microdiafiltration and (b) extracting the hydrophobic protein from the retentate obtained in the above-mentioned step (a) by microfiltration using a buffer containing at least one detergent. According to another specific example, the extraction step contains, additionally to the above-mentioned steps (a) and (b) the step (c) wherein the filtrate obtained from above-mentioned step (b) is subjected to microfiltration and/or microdiafiltration using a 0.2 μm pore size microfiltration cassette.

The hydroxyapatite column chromatography step (iii) according to the present invention is not restricted in a specific way and includes all hydroxyapatite chromatography materials and protocols known to the skilled person.

In a specific example of the method as defined above the hydroxyapatite column material used in the hydroxyapatite column chromatography is commercially available such as HA ULTROGEL™.

The buffers usable in the hydroxyapatite column chromatography step (vi) of the above-defined method are not specifically limited and include any buffer known in the art which can be used in hydroxyapatite column chromatography. In a specific example of the present invention, the buffer used in said hydroxyapatite column chromatography is a sodium phosphate-buffer, having a concentration in the range of about 1 mM to about 600 mM and a pH-value in the range of about 6 to about 8.

According to a further example of the present invention, in the method as defined above, the filtrate obtained from said extraction step (ii) is subjected to ion exchange filtration using a membrane adsorber, prior to hydroxyapatite column chromatography step (iii). Suitable adsorbers are available from Pall Inc. or Sartorius. In a specific example of the present invention, the anion-exchange membrane adsorber used is Mustang Q (Pall).

According to one example of the method as defined above, the hydrophobic protein to be purified is recombinant synthetic Lyme Antigen (rSLA).

In a further example of the method according to the present invention, the host cells containing said hydrophobic protein provided in step (i) are host cells selected from the group consisting of E. coli, but any host cell capable of expressing recombinant hydrophobic proteins, like yeast cells, plant cells, insect cells, avian cells or mammalian cells can be subjected to the described process.

According to a specific example of the present invention, the detergent used in the method as described above may be anionic, such as cholic acids and derivatives thereof, N,N-dimethyldodecylamine N-oxide, sodium 1-alkylsulfonates, N lauroylsarcosine or fatty acid salts, cationic, such as alkyl trimethyl ammonium bromide and derivatives thereof or benzalkonium chloride, zwitterionic, such as dodecyl betaine, alkyl dimethylamine oxide and derivatives thereof or 3-(N, N-dimethylalkylammonio)propanesulfonates, or nonionic, such as octylphenol ethoxylates, polyoxyethylene sorbitan monooleates, alkyl poly(ethylene oxides) and derivatives thereof, alkyl polyglucosides or fatty alcohols.

According to another specific example of the present invention, the detergent used in the method as defined above is commercially available such as an octylphenol ethoxylate (e.g. TRITON™ X100 or TRITON™ X114), a polyoxyethylene sorbitan monooleate (e.g. TWEEN™ 80) or an N-alkyl-N,N-dimethyl-3-amino-1-propane sulfonate (e.g. ZWITTERGENT™ 3-14).

In another example of the method as defined above, the buffer used in step (ii) contains octylphenol ethoxylate (Triton™ 100) as a detergent.

According to a further example of the present invention, in the method as defined above, a microfiltration and/or microdiafiltration step is performed after the extraction step (ii), for example using a 0.2 μm pore size microfiltration cassette.

The operating temperatures used in the method according to the present invention do not underlie a specific limitation, and can be, for example, at about room temperature or below room temperature, such as in the range of about 0 to about 15° C.

According to one example of the method as defined above, highly purified lipidated protein is obtainable from cells comprising the steps of:
  (i) providing cells containing said lipidated protein;
  (ii) homogenizing said cells;
  (iii) subjecting the such obtained homogenate to micro (dia)filtration comprising the steps of:
    (a) concentrating said homogenate by microfiltration;
    (b) washing the biomass by microdiafiltration, thereby obtaining a microdiafiltrate-1 and a microdiaretentate-1;
    (c) extracting the lipidated protein from said microdiaretentate-1 by microdiafiltration using a buffer containing a detergent thereby obtaining a microdiafiltrate-2 and a microdiaretentate-2;
  (iv) subjecting said microdiafiltrate-2 containing the extracted lipidated protein to ion exchange chromatography, the eluent thereof containing the purified lipidated protein;
  (v) subjecting the eluent obtained from the ion exchange chromatography in step (iv) to anion exchange filtration for residual endotoxin removal; and
  (vi) subjecting the such obtained protein solution containing the lipidated protein to hydroxyapatite (HA) column chromatography.

According to a specific example of the method as defined above, highly purified recombinant Synthetic Lyme Antigen (rSLA) is obtainable from cells comprising the steps of:
  (i) providing cells containing said rSLA;
  (ii) homogenizing said cells;
  (iii) subjecting the such obtained homogenate to micro (dia)filtration comprising the steps of:
    (a) concentrating said homogenate by microfiltration;
    (b) washing the biomass by microdiafiltration, thereby obtaining a microdiafiltrate-1 and a microdiaretentate-1;
    (c) extracting rSLA from said microdiaretentate-1 by microdiafiltration using a buffer containing a detergent thereby obtaining a microdiafiltrate-2 and a microdiaretentate-2;
  (iv) subjecting said microdiafiltrate-2 containing the extracted rSLA to ion exchange chromatography, the eluent thereof containing the purified rSLA;
  (v) subjecting the eluent obtained from the ion exchange chromatography in step (iv) to anion exchange filtration for residual endotoxin removal; and
  (vi) subjecting the such obtained protein solution containing rSLA to hydroxyapatite (HA) column chromatography.

The above-defined examples of the method according to the present invention may additionally contain a microfiltration and/or microdiafiltration step after the extraction step (iii) (c), for example using a 0.2 μm pore size microfiltration cassette.

A further aspect of the present invention relates to a pharmaceutical composition, comprising the hydrophobic protein, obtainable by the above-defined method and at least a pharmaceutically acceptable carrier.

In another example of the present invention the pharmaceutical composition as defined above comprises a therapeutically effective amount of the hydrophobic protein purified by the method as defined above and optionally one or more additional components selected from the group consisting of a pharmaceutically acceptable carrier, a pharmaceutically acceptable salt, an auxiliary agent, a diluent and a solvent, or any combination thereof.

According to one example, the pharmaceutical composition as defined above comprises a lipidated protein, obtainable by the method as defined above and at least a pharmaceutical acceptable carrier and/or diluent.

In another specific example of the pharmaceutical composition as defined above, said pharmaceutical composition comprises rSLA, obtainable by the method as defined above and at least a pharmaceutically acceptable carrier and/or diluent.

The method of the present invention provides access to a highly purified hydrophobic protein, which can be advantageously used in preparations and used for pharmaceutical and diagnostic applications. In particular, the application of a detergent for solubilizing said hydrophobic protein and the successive removal of said detergent by hydroxyapatite column chromatography under those parameters specified in the present invention enables a surprisingly efficient and versatile purification of hydrophobic proteins and results in advantageously low amounts of impurities originating from cultivation of cells used for generating said hydrophobic protein and from the purification process.

The present invention will be further illustrated in the following examples, without any limitation thereof.

EXAMPLES

Example 1

Concentration of TRITON™ X100 for rSLA Extraction

Efficacy of extraction of rSLA from the cell membranes was tested using different TRITON™ X100 concentrations. Since solubilization of E. coli proteins and membrane lipids increase as a consequence of elevated TRITON™ X100 concentrations, a negative impact on the efficiency of succeeding purification steps might occur. Therefore, in order to find the optimal TRITON™ X100 concentration, fractions with different TRITON™ X100 concentrations were compared, before and after the anion exchange chromatography procedure, which was potent in removing the bulk of E. coli proteins.

Following concentrations of TRITON™ X100 in the resuspension buffer were tested (0.5%, 1.0%, 1.5%, 2.0% and 3.0%). The pellet was resuspended in the respective TRITON™ X100-containing buffer and stirred for 1 hour at RT. The suspension was centrifuged at 16.000 rpm (with a JA20-rotor in a Beckman centrifuge) for 20 minutes. The resulting supernatant was subsequently analyzed and a sample aliquot was further purified with an anion exchange resin in order to eliminate the bulk of E. coli proteins. This was necessary to assess the influence of TRITON™ X100 concentration on the purity of rSLA after the anion exchange chromatography. The efficacy of the extraction procedure, measured by determination of total protein and rSLA content, using different TRITON™ X100 concentrations is listed in Table 1.

TABLE 1

The anion exchange resin DE-53 removed most of the E. coli proteins from the centrifuged supernatants after TRITON ™ X100 extraction. Since binding of rSLA protein to the DE-53 resin was minimal, it was left, to a high degree, in the supernatant fractions. Percentage of rSLA was maximal in the extracts with 1.0-1.5% TRITON ™ X100 (bold) after DE53 batch incubation.

| Probe OspA/110803 | Total protein content (μg/ml) | rSLA content (μg/ml) | rSLA/protein in % |
|---|---|---|---|
| Original material | 16215 | 1018.4 | 6.3 |
| SN 0.5% TX | 2169 | 403.8 | 18.6 |
| SN 1.0% TX | 2117 | 448.4 | 21.2 |
| SN 1.5% TX | 2525 | 467.1 | 18.5 |
| SN 2.0% TX | 2369 | 440.3 | 18.6 |
| SN 3.0% TX | 2512 | 463.2 | 18.4 |
| SN DE53, 0.5% TX | 439 | 267.0 | 60.8 |
| SN DE53, 1.0% TX | 318 | 251.9 | 79.2 |
| SN DE53, 1.5% TX | 373 | 281.6 | 75.5 |
| SN DE53, 2.0% TX | 307 | 223.5 | 72.8 |
| SN DE53, 3.0% TX | 433 | 313.9 | 72.5 |

SN: supernatant after centrifugation of the extract; SN DE-53: supernatant from the DE-53 resin batch incubation After the purification with the DE-53 resin, total protein levels were diminished, but rSLA-protein was significantly enriched, compared to the supernatant after the centrifugation of the extract. The percentage of the rSLA from total protein (measured in μg/ml) in the solution reached a level of about 75% to almost 80% at TRITON™ X100-concentrations of 1.5 and 1.0% respectively. The latter concentration was favored due to the slightly improved yield of rSLA. To definitely decide what TRITON™ X100 concentration was preferred, a Coomassie stained PAGE was performed (see, FIG. 1).

Example 2

Comparison of Microfiltration Versus Centrifugation

Figure 2:
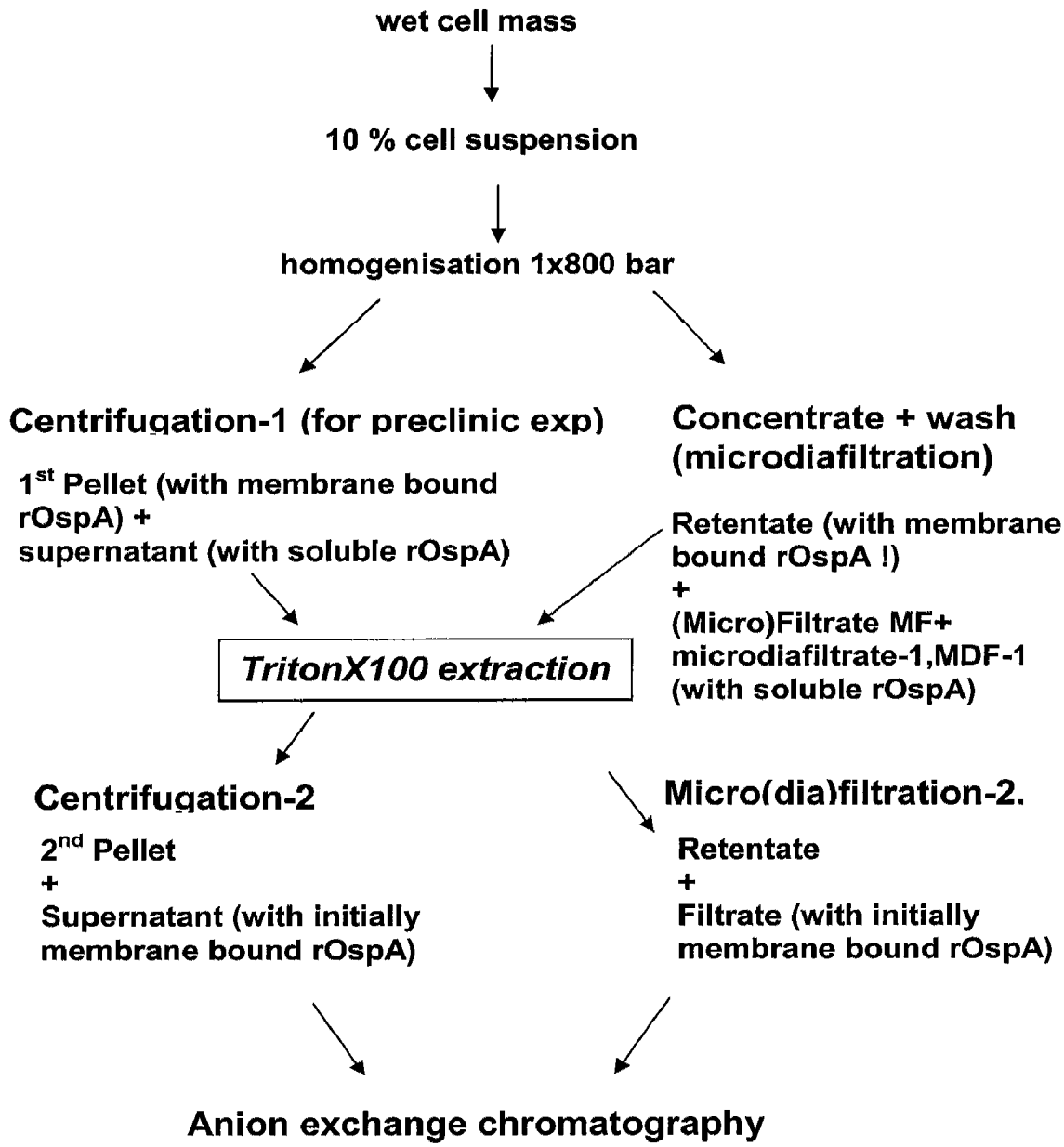
FIG. 2 shows a comparison of purification protocols using centrifugation and microfiltration.

Centrifugation of turbid solutions is generally the first choice for cell debris separation. With regard to establishing an industrial production scale process, alternative methods seem to be a good investment due to high cost of industrial scale centrifuges and laborious handling of the working fluids. An alternative separation strategy is provided by microfiltration. Therefore, a purification strategy, in which centrifugation is substituted by microfiltration was investigated (see, FIG. 2.)

Comparison of Yield and Purity of rSLA Purified by Either Microfiltration or Centrifugation The following data listed in table 2 demonstrated that microfiltration can substitute for centrifugation. Therefore microfiltration can effectively be integrated in the purification process for rSLA hybrid proteins.

TABLE 2

Purities of rSLA for all 3 chimeras are given. Purification was performed by either centrifugation or microfiltration. The rate of yields and purity in microfiltrated rSLA was even higher than in the preclinical lots which were purified by use of centrifugations.

| rSLA chimaera | Micro-filtrated rSLA | | | Centrifuged rSLA, preclinical production | | |
|---|---|---|---|---|---|---|
| | 6/4 | 1/2 | 5/3 | 6/4 | 5/3 | 1/2 |
| Protein (µg/ml, BCA) | 523.0 / 397.0 | 707.0 | 1121.0 | 393 | 360 | 333 |
| Purity in % | 98.5*[1] / 99.4*[2] | 98.7 | 98.6 | 93.4 / 86.5 | 97.3 | 97 |
| rSLA total - in mg (from 50 g wet cell mass) | 26.8 / 15.4 | 71.9 | 104.3 | — | — | — |
| rSLA total - in mg (from 125 g wet cell mass) | — | — | — | 51.9 / 27.7 | 99.1 | 93.0 |
| Yield (mg rSLA/g wet cell mass) | 0.54 / 0.42 | 1.44 | 2.09 | 0.42 / 0.22 | 0.79 | 0.74 |
| LAL (EU/ml) | <1.5 | <1.5 | <1.5 | <1.5 | <1.5 | <1.5 |
| E. coli DNA | — | — | — | neg | neg | neg |
| E. coli protein (µg/ml) | — | — | — | 3.77 | <1.0 | <1.0 |
| Benzonase-ELISA (µg/ml) | — | — | — | <1.3 | <1.3 | <0.3 |
| TRITON ™ X100 content (%) | — | 0.00006 | 0.00006 | 0.00076 | 0.00017 | 0.00008 |
| cfu/ml | —** | —** | —** | 0 | 0 | 0 |

*[1] first purification with 18% buffer B during HA chromatography;
*[2] second with 18% + 25% buffer B,
**not determined, samples were sterile filtered for immunogenicity tests in mice.

Integrating microfiltration into the purification process yields highly pure rSLA for all 3 chimeric constructs. To prove that immunogenic properties from microfiltrated rSLA were the same as rSLA from preclinical lots, immunogenicity studies in mice from all 3 rSLA chimeras were performed.

Figure 3:
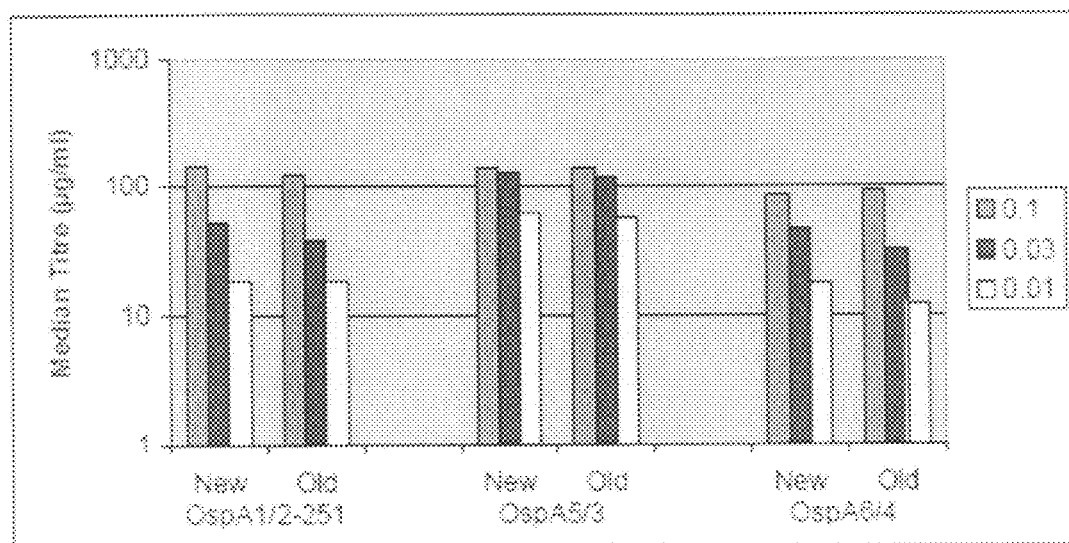
FIG. 3 shows a comparison diagram of the generation of high antibody-titer induced by rSLA, purified by either centrifugation or microfiltration. Groups of 10 mice were subcutaneously immunized (day 0) with 0.1 µg, 0.03 µg and 0.01 µg of rSLA per mouse. For generating rSLA-specific antibodies, a single dose was sufficient in each case. A significant response was detectable after 3 weeks (day 21). All 3 chimeric rSLA-proteins, purified by either microfiltration or centrifugation, were compared in parallel. "New", indicated use of microfiltration, "Old" indicated centrifuged rSLA. Immunogenic properties were equivalent for both preparations. Therefore, microfiltration did not adversely affect immunogenicity of rSLA.

Comparison of Immunogenicity of Purified rSLA Using Centrifugation or Microfiltration To verify that the immunogenicity of rSLA, purified in a process where centrifugation was substituted by microfiltration, was not diminished, products from both purification strategies were compared in an immunogenicity study. The efficiency of generating high antibody titer with material from microfiltrated rSLA ("New") was equivalent to that purified by use of centrifugation ("Old") (see, FIG. 3)

Example 3

The Process of Microfiltration

The microfiltration was performed in two steps:
1) At the beginning of the microfiltration process, concentration of the homogenate was performed by microfiltration, followed by washing the biomass with TRIS-buffer (=microdiafiltration-1).
2) Subsequently, rSLA was extracted by a TRITON™ X100 containing buffer from the microdiaretenate by microdiafiltration.

For the first experimental microfiltration, lipidated rSLA serotype 6/4 was used. In principle microfiltration was performed in order to remove small soluble proteins and to concentrate the sample. For the initial microfiltration, a concentration factor of 2 has been established to be optimal. This concentration factor does not further compromise succeeding purification steps. A concentration factor of 4 was used in earlier experiments but later abandoned because of too high viscosity of the microdiaretentate-1. After concentration by microfiltration, a microdiafiltration with 3 volume changes of diafiltration buffer 1 (without TRITON™ X100) was performed. A proportion of soluble proteins were washed out.

TRITON™ X100 Extraction of rSLA by Microdiafiltration

Figure 4:
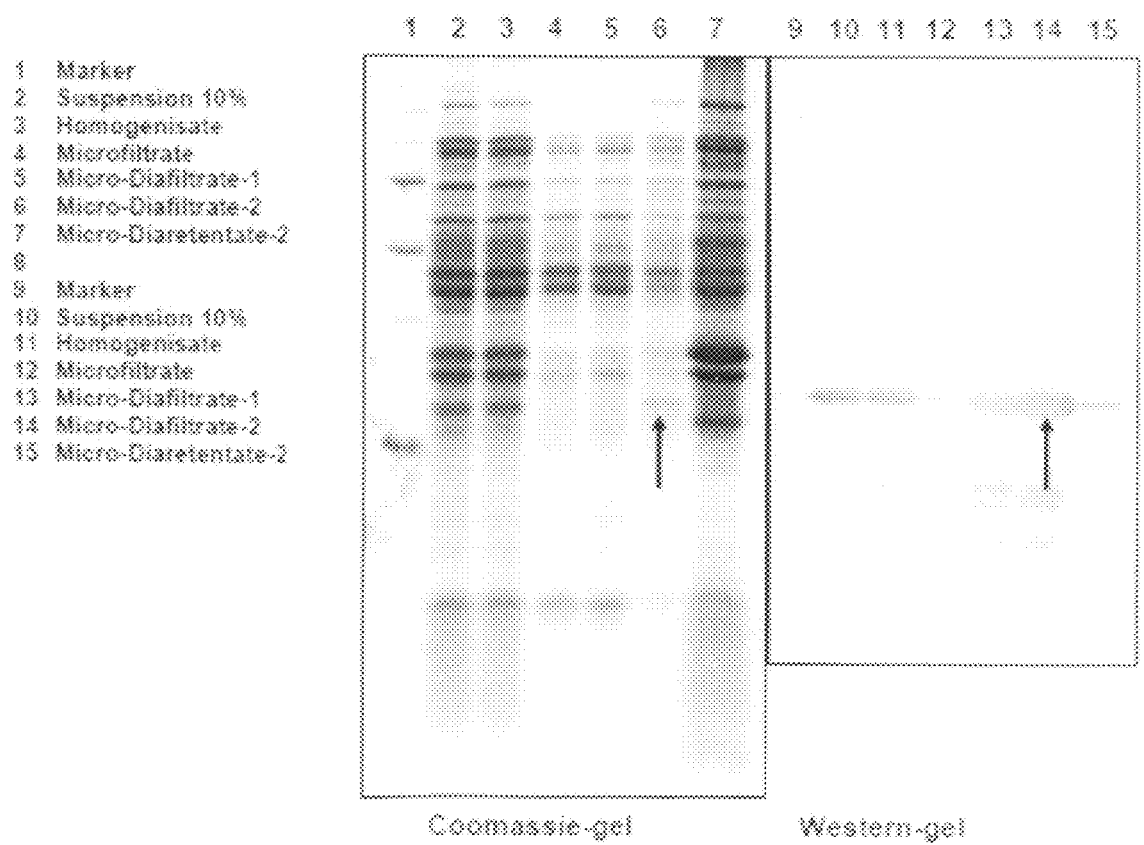
FIG. 4 shows a Coomassie gel and a western blot verifying operability of extraction of rSLA by microdiafiltration using TRITON™ X100. Bacterial cells producing rSLA-serotype 6/4 were suspended and homogenized (lanes 2, 3, 10 and 11). First, concentration of the biomass was performed by microfiltration, followed by washing the concentrate with 3 volume changes of Tris buffer. Small soluble proteins were washed out and were found in the microfiltrate (lane 4). Loss of rSLA was minimal, confirmed by western blotting (lane 12). The concentrated retentate, containing most of the target protein, since the diafiltrationbuffer-1 did not contain any detergents. The microdiafiltrate-1 confirmed removal of proteins by washing (lane 5). A small portion of soluble rSLA was lost (lane 13) into the filtrate. By changing to the TRITON™ X100 containing buffer (diafiltrationbuffer-2), a significant amount of rSLA was detectable in the microdiafiltrate-2 (lane 6 and 14, see arrows).

Following microdiafiltration-1, the extraction procedure takes place. After concentration of the microdiaretentate-1, TRITON™ X100 was added to a final concentration of 1.5%. The biomass was agitated on a magnetic stirrer. An incubation time of 30 minutes was sufficient for extraction. Microdiafiltration-2 (MDF-2) was then carried out with the extraction buffer, containing TRITON™ X100. The microdiafiltrate-2, contained the extracted rSLA (FIG. 1, FIG. 4). A constant TRITON™ X100 concentration during volume changes with microdiafiltration buffer was important to allow extraction and keep rSLA solubilized in the filtrate.

Figure 5:
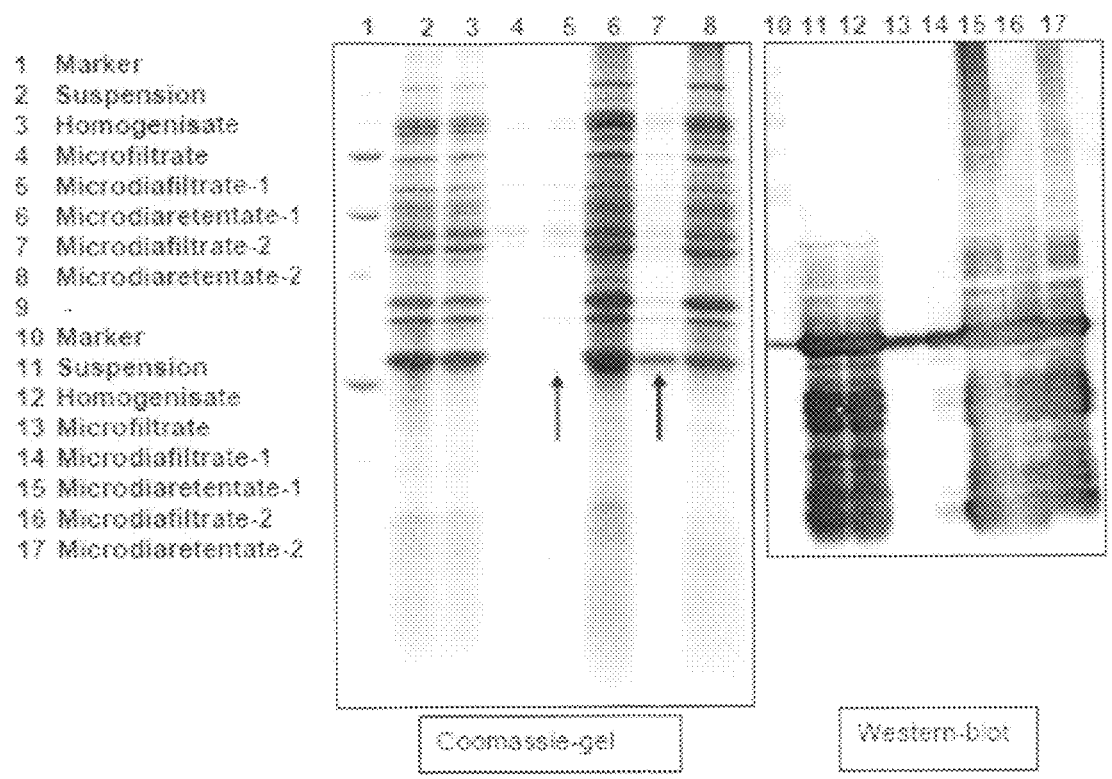
FIG. 5 shows a Coomassie gel and a western blot, verifying that the extraction of rSLA of serotype 1/2 by microdiafiltration using TRITON™ X100 was reproducible. This experiment was performed analogous to the extraction of rSLA of serotype 6/4. The Coomassie stained gel and western blotting verified the results obtained in the first experiment that rSLA of serotyp1/2 can be effectively extracted by TRITON™ X100 using microfiltration, indicated by accumulation of the target protein in the microdiafiltration buffer-2 (lane 7, see arrow). This was not the case in the microdiafiltration buffer-1 (lane 5, see arrow).

The equivalent procedure was performed with lipidated rSLA serotype 1/2 to reproduce the results obtained with the rSLA serotype 6/4 and to verify the methodology of rSLA extraction by microfiltration (see, FIG. 5)

Figure 6:
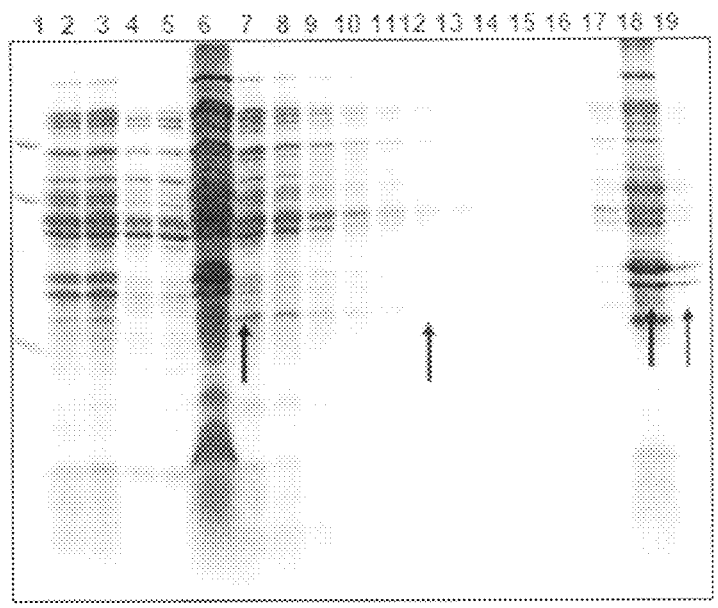
FIG. 6 shows a photograph of a gel for determination of the number of volume changes with microdiafiltration buffer-2 (+TRITON™ X100) for quantitatively extracting rSLA from the initial microdiaretentate. The suspension and the homogenizate are represented by lane 2 and 3. Microfiltration removed impurities without significant loss of rSLA (lane 4). The same was true for the microdiafiltrate-1 (lane 5). The target protein was present in the microdiaretenate-1 (lane 6). Microdiafiltration with TRITON™ X100 containing buffer solubilized rSLA, which was found in the microdiafiltrate-2 (lane 7, arrow). After each volume change with microdiafiltrationbuffer-2, a sample was taken for SDS-gel analysis. The quantity of the target protein slightly decreased after each volume change. After about 6 volume-changes with microdiafiltration-buffer-2, rSLA was extracted almost quantitatively and extraction by microdiafiltration was stopped at this point (lane 12; arrow). Finally all 10 fractions were pooled (lane 17). For comparison, the microdiaretenate-2 was loaded onto the gel in concentrated form and 1 to 10 diluted, in order to demonstrate quantitative extraction (see arrows).

For optimization of the extraction procedure, the number of volume changes (VC) with microdiafiltrationbuffer-2, necessary for quantitative extraction of rSLA was investigated. A sample was collected from the microdiafiltrate-2 after each volume change (VC), and analyzed for the rSLA content by SDS PAGE. (FIG. 6).

The optimization experiment, showed that six volume changes with diafiltration buffer-2 was sufficient for quantitative extraction of rSLA.

Example 4

Optimization of Microfiltration by Choosing the Correct Cassette Pore-Size

To evaluate optimal removal of the bulk of *E. coli* proteins and sufficient retention of the target protein, microfiltration cassettes with two different pore sizes were studied. For these microfiltration experiments, polyethersulfone membranes (supor TFF) from Pall Inc., were used. The dimension (0.1 m² filtration area) is adequate for laboratory scale volumes. Two pore sizes, 0.2 μm and a 1000 kD were compared. The fractions were analyzed by Coomassie stained PAGE-gels and western blot analyses (see, FIG. 7).

The equivalent procedure was performed with the 1000 kD membrane from Pall Inc. with identical filtration area. Retention of E. coli proteins with the 1000 kD membrane was significantly higher (see, FIG. 8, lanes 11 and 13). As a consequence, the loss of rSLA in the microdiafiltrate was minimal (lane 12 and 14). Extraction of rSLA with TRITON™ X100 was possible (lane 16), but incomplete, indicated by still high amounts of rSLA in the microdiaretentate-2, MDR-2 (lane 15). Additionally the depletion of bulk proteins from E. coli in the MDF-2 was far less efficient, as it was accomplished with the 0.2 μm pore size membrane (see, FIG. 7).

Figure 7:
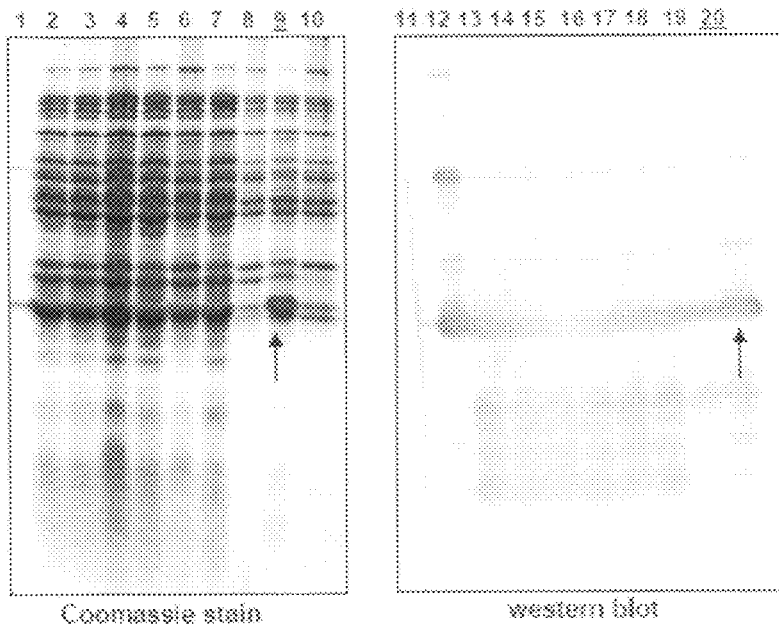
FIG. 7 shows a photograph of a Coomassie gel and a western blot of the experiments using a 0.2 µm membrane (Gel 1): Efficacy of rSLA enrichment by TRITON™ X100 extraction during microfiltration. The microretentate (MR) was concentrated by a factor of 2 to reduce working volumes (lane 4). The amount of rSLA lost in the microfiltrate (MF) was detectable but moderate (lane 5). Microdiafiltration exhibited the same loss of target protein but enough rSLA was still present worth of purifying it (lanes 6 and 7). Enrichment of rSLA and separation from *E. coli* proteins was efficient with this 0.2 µm pore size membrane in the microdiafiltrate-2 (MDF-2), as indicated by the arrow. Only minimal amounts of rSLA were found at the respective size in the microdiaretentate-2 (lane 8).
Figure 8:
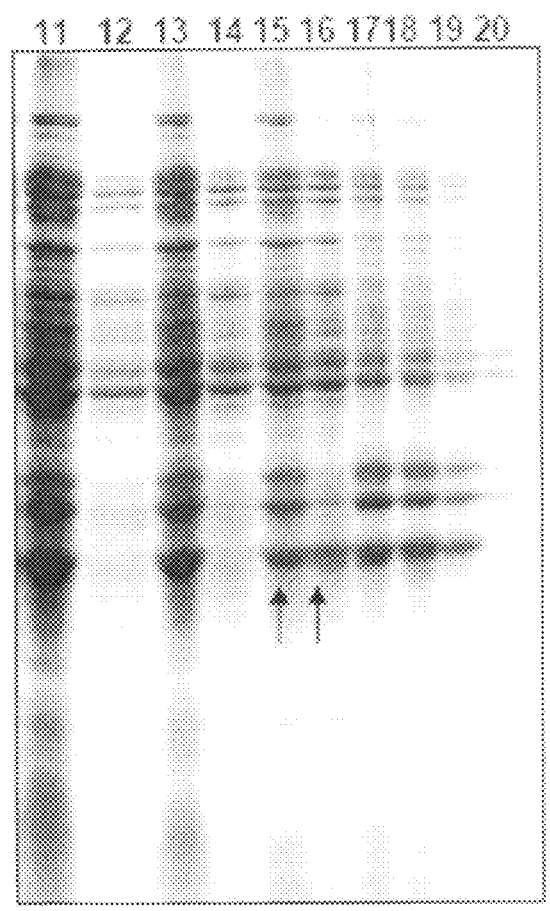
FIG. 8 shows a photograph of a gel of the experiments using a 1000 kD membrane (Gel 2): Retention of *E. coli* proteins with the 1000 kD membrane was significantly higher (lane 11 and 13). As a consequence, the loss of rSLA in the microdiafiltrate was minimal (lane 12 and 14). Extraction of rSLA with TRITON™ X100 was possible (lane 16), but incomplete, indicated by still high amounts of rSLA in the microdiaretentate-2, MDR-2 (lane 15). Additionally the depletion of bulk proteins from *E. coli* in the MDF-2 was far less efficient, as it was accomplished with the 0.2 µm pore size membrane (cf.

Extraction of rSLA was more efficient with the 0.2 μm pore size membrane, which consequently was used for all future microfiltration experiments (cf. FIG. 7, lanes 9 and 20).

Example 5

Detergent Removal by Hydroxyapatite

Hydroxyapatite (HA) ULTROGEL™ Chromatography

After the negative chromatographic step with DE-53, most E. coli proteins were removed from the rSLA solution. For a human vaccine, purity is of top priority. Therefore a final polishing step to remove residual bacterial cell proteins was necessary.

HA ULTROGEL™ has some advantages. HA exhibits excellent chemical and mechanical stability, a broad pH-value-working range, the possibility to store it at room temperature and offers ease of regeneration and depyrogenation with 0.1 N to 1 N NaOH-solution.

One central task during development of the HA chromatography was to remove the detergent TRITON™ X100 and to yield highly pure rSLA. Initial trials at the beginning of the process development verified that detergent removal works. This method turned out to be very efficient in removing TRITON™ X100 from the solution, which was necessary for extraction and solubilization of rSLA. Purification of all 3 rSLA hybrid proteins revealed minimal amounts of residual TRITON™ X100 after the HA step. The second strategy during development of the HA chromatography procedure was to improve the purity of the target protein by modifying the elution conditions. The approach was to increase the stringency of the elution conditions by applying prolonged steps of increased ionic strength.

The Chromatographic Process with Hydroxyapatite ULTROGEL™

This example describes the HA chromatography procedure including proper preparation of hydroxyapatite before use. Hydroxyapatite ULTROGEL™ (HA) was packed into a column in order to perform a column chromatographic process, which can be controlled by the AKTA Explorer control system (GE Healthcare). For long term storage, HA was put into 20% EtOH plus 1 M NaCl. For regeneration and depyrogenation of the HA-gel, the column was flushed with 2 column volumes of 0.5 N NaOH. To start with the chromatography procedure, one had to rinse the column with a set of different fluids. First, the packed column was flushed with 2 column volumes (CV) of water (WFI, water for injection) followed by 2 CV's of 0.5 N NaOH and finally 8 CV's of WFI again, which comprised the initial rinsing procedure. This guaranteed that all residual contaminations and possible pyrogenic substances were removed at the start of the chromatographic process. The succeeding equilibration procedure consisted of 3 rinsing steps. The resin was flushed with 1 CV of 10 mM sodium phosphate-buffer at pH=6.8 (equilibration buffer), followed by 2 CV's of 500 mM sodium phosphate-buffer (elution buffer or buffer-B), pH=6.8 and again 3 CV's of equilibration buffer. The intermediate 500 mM step simulated the maximum ionic strength applied in this chromatography step. This assure that under maximum elution conditions, residual protein was washed out from the resin before applying the protein solution.

Figure 9:
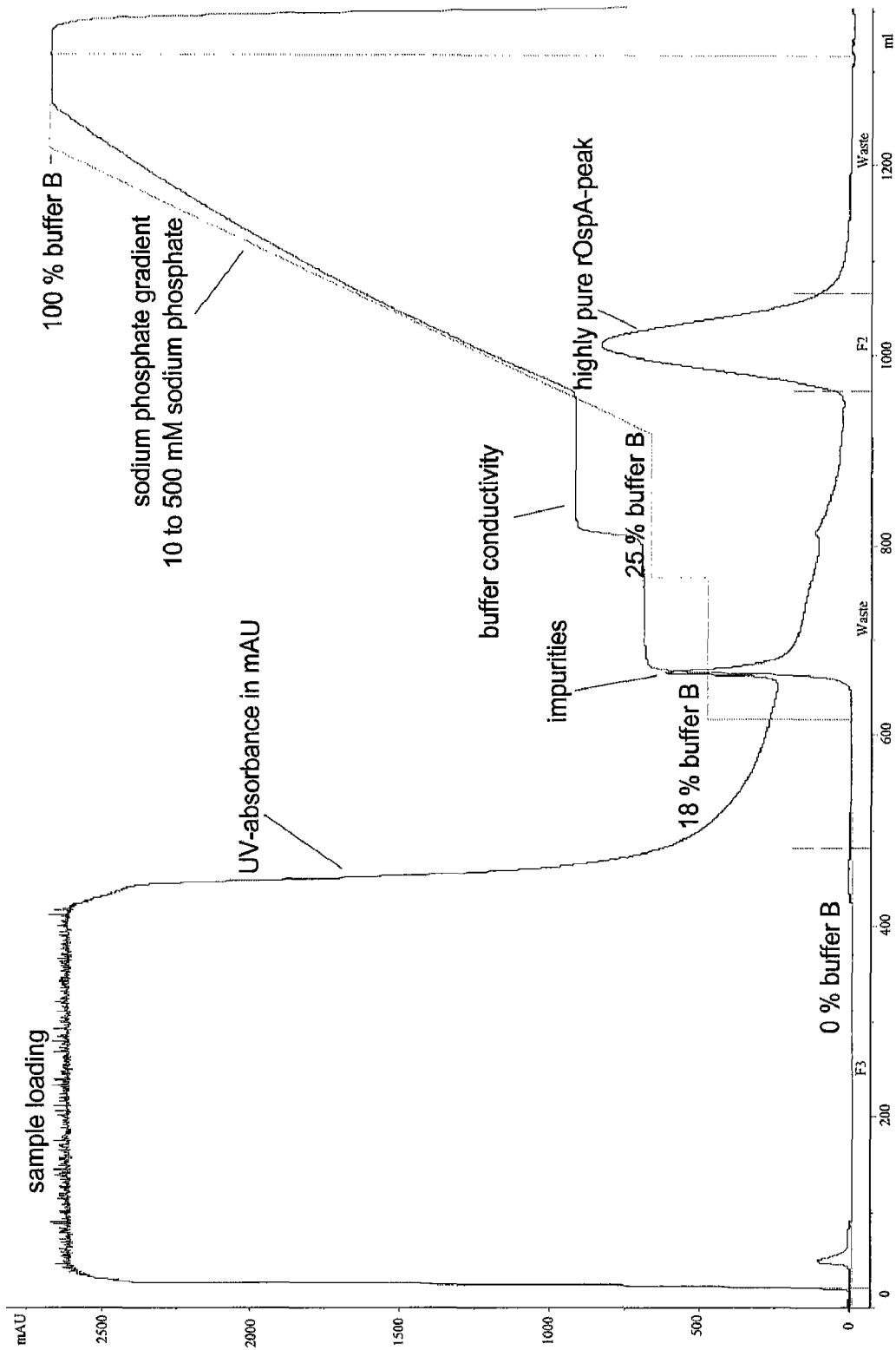
FIG. 9 shows a chromatogram of the purification scheme with the HA ULTROGEL™ for chimeric rSLA serotype 5/3. This purification scheme is, in principle, applicable for all 3 rSLA chimeras. The initial first large peak characterizes sample application. At the beginning of sample loading, the strong UV signal was largely due to TRITON™ X100 in the solution. After sample loading, the UV-line should drop off to levels close to zero. The elution step was started subsequently, with a two step mode, 18% and 25% buffer-B step, indicated by the green line. Thereafter, a linear gradient was continued to 100% buffer B. Both steps (18% and 25%) showed removal of *E. coli* proteins. The protein peak at 18% buffer B was clearly visible, the peak at 25% buffer B was only a small hump (arrow). Depletion of residual *E. coli* proteins allowed for very high purity of rSLA.
Figure 10:
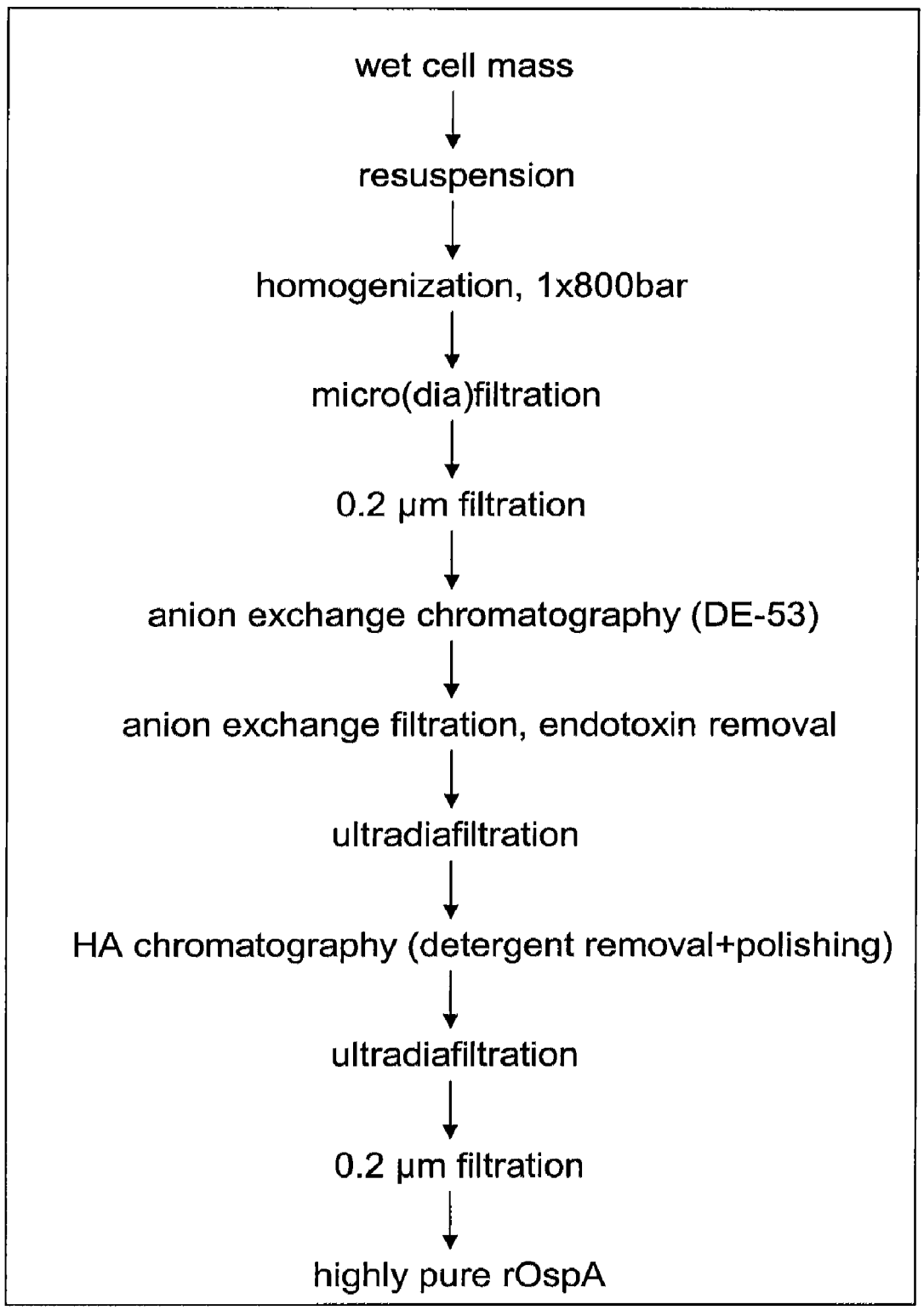
FIG. 10 shows a flow chart of the processing steps applied for rSLA purification.

At this point, the column was ready for sample application. The amount of sample defined the loading time (speed of loading is given in ml per minute; high speed loading is limited by the system-pressure, –maximum 6 bar). Proteins were detected by UV light at 280 nm. During sample loading, the loading peak was very high. This reflected the fact that TRITON™ 100 was dissolved in the protein solution, which was known to absorb at 280 nm as well (see, FIG. 9). After completion of sample loading, the column was again flushed with equilibration buffer. Flushing continued until the 280 nm signal remained unchanged. This happened after about 3 CV's of equilibration buffer.

After the UV-signal stabilized at the base line, the elution program was started. It consisted of a few separate steps. First, continuous addition of elution buffer, which gradually increased the ionic strength and lead to depletion of impurities visible in the chromatogram by a small peak at about 18% of elution buffer ("buffer B"). This step was put on hold until the UV-line of the protein peak was at the base line again. At 25% buffer B the gradient was put on hold again until the UV-signal met the base line level again before the linear gradient was continued. Generally at about 30-35% buffer B, the rSLA began to elute and formed a peak, which discontinued at about 60% buffer B. This fraction was collected in a separate vial, which now contained the purified product.

For rSLA elution, the window of the percentage of buffer B was chosen to be narrow (35-55% buffer B instead of 30-60%). Small losses of target proteins could not be avoided, but high purity of the end product was obtained in all 3 cases of chimeric rSLA.

Example 6

Specific Example of a Complete rSLA Purification Protocol

According to a specific example the method of the present invention was carried out as follows:

A wet cell mass of E. coli, which expressed rSLA, was resuspended and homogenized to disrupt the bacterial cells. This cell suspension was then microfiltrated and washed (microdiafiltrated) with Tris buffer in order to wash out tiny particles and soluble E. coli proteins. Extraction was performed by the TRITON™ M X100-containing second microdiafiltation buffer, which solubilized rSLA from E. coli cell membranes. This protein solution was then 0.2 μm filtered in order to keep the subsequent anion exchange column free from germs. The anion exchange chromatography was used as a negative chromatography step. E. coli proteins were bound to a large degree. In contrast, rSLA largely passed through the column and was therefore found in the flow through. The flow through, containing the target protein, was then passed through a membrane adsorber (anion exchange filtration) for residual endotoxin removal. In order to change the buffer conditions for a subsequent final chromatography step, an ultrafiltration was performed. The protein solution with large amounts of rSLA and TRITON™ X100, was then loaded onto a HA column, which depleted residual E. coli proteins and TRITON™ X100. A final ultrafiltration was performed to transfer rSLA into a physiologic buffer system. A final sterile filtration finished the purification process.

What is claimed is:

1. A method for purifying recombinant synthetic Lyme antigen (rSLA) comprising the steps of:
   (i) subjecting a homogenate of cells containing the rSLA to microdiafiltration comprising the steps of:
      (a) concentrating said homogenate by microfiltration;
      (b) washing the biomass by microdiafiltration, thereby obtaining a microdiafiltrate-1 and a microdiaretentate-1;
      (c) extracting the rSLA from said microdiaretentate-1 by microdiafiltration using a buffer containing a detergent thereby obtaining a microdiafiltrate-2 and a microdiaretentate-2;
   (ii) subjecting said microdiafiltrate-2 containing the extracted rSLA to ion exchange chromatography, the eluent thereof containing the purified rSLA;
   (iii) subjecting the eluent obtained from the ion exchange chromatography in step (ii) to anion exchange filtration for residual endotoxin removal; and
   (iv) subjecting the such obtained protein solution containing the rSLA to hydroxyapatite (HA) column chromatography.

2. The method according to claim 1, wherein, prior to step (i), the cell homogenate is washed using a suitable buffer selected from the group consisting of: Tris-buffer, HEPES buffer, citrate buffer, and phosphate buffer.

3. The method according to claim 1, wherein, prior to step (iv), the filtrate obtained from said extraction step (ii) is subjected to ion exchange chromatography.

4. The method according to claim 1, wherein, prior to step (iv), the filtrate obtained from said extraction step (ii) is subjected to anion exchange filtration using a membrane adsorber.

5. The method according to claim 1, wherein the cells containing said rSLA are host cells selected from the group consisting of E. coli, yeasts, plant cells, insect cells, avian cells or mammalian cells.

6. The method according to claim 1, wherein the buffer used in step (i)(c) contains a detergent selected from the group consisting of anionic detergents, cationic detergents, zwitterionic detergents and non-ionic detergents,
   wherein the anionic detergents are selected from the group consisting of cholic acids and derivatives thereof, N,N-dimethyldodecylamine N-oxide, sodium 1-alkylsulfonates, N lauroylsarcosine or fatty acid salts;
   wherein the cationic detergents are selected from the group consisting of alkyl trimethyl ammonium bromide and derivatives thereof or benzalkonium chloride;
   wherein the zwitterionic detergents are selected from the group consisting of dodecyl betaine, alkyl dimethylamine oxide and derivatives thereof or 3-(N,N-dimethylalkyl-ammonio)-propanesulfonates; and
   wherein the non-ionic detergents are selected from the group consisting of octylphenol ethoxylates, polyoxyethylene sorbitan monooleates, alkyl poly(ethylene oxides) and derivatives thereof, alkyl polyglucosides or fatty alcohols.

7. The method of claim 6, wherein the detergent is present in an amount from about 0.5% to about 3.0%.

8. The method of claim 6, wherein the detergent is present in an amount from about 1% to about 1.5%.

9. The method according to claim 1, wherein the buffer used in step (i)(c) is Tris-buffer.

10. The method according to claim 1, wherein the buffer used in step (i)(c) contains octylphenol ethoxylate as a detergent.

11. The method according to claim 1, wherein, after step (i)(c), a microfiltration and/or microdiafiltration step is performed using a 0.2 µm pore size microfiltration cassette.

12. The method according to claim 1, wherein the buffer concentrations are in a range from about 0.1 mM to about 1.0M.

13. The method of claim 1, wherein the buffer concentrations are in a range from about 1.0 mM to about 600 mM.

14. The method of claim 1, wherein the pH of the buffers ranges from about 3.0 to about 10.0.

15. The method of claim 1, wherein the pH of the buffers ranges from about 6.0 to about 8.0.

16. The method of claim 1, wherein the method is carried out at room temperature.

17. The method of claim 1, wherein the method is carried out at a temperature from about 0° C. to about 15° C.

18. A method for purifying recombinant synthetic Lyme antigen (rSLA) from a cell comprising the steps of:
   (i) providing cells containing said rSLA;
   (ii) homogenizing said cells;
   (iii) subjecting the such obtained homogenate to microdiafiltration comprising the steps of:
      (a) concentrating said homogenate by microfiltration;
      (b) washing the biomass by microdiafiltration, thereby obtaining a microdiafiltrate-1 and a microdiaretentate-1;
      (c) extracting rSLA from said microdiaretentate-1 by microdiafiltration using a buffer containing at least octylphenol ethoxylate, thereby obtaining a microdiafiltrate-2 and a microdiaretentate-2;
   (iv) subjecting said microdiafiltrate-2 containing the extracted rSLA to anion exchange chromatography, the eluent thereof containing the purified rSLA;
   (v) subjecting the eluent obtained from the anion exchange chromatography in step (iv) to anion exchange filtration for residual endotoxin removal; and
- (vi) subjecting the such obtained protein solution containing rSLA to hydroxyapatite (HA) column chromatography.

19. The method according to claim 18, wherein, prior to step (iii)(c), the cell homogenate is washed using a suitable buffer selected from the group consisting of: Tris-buffer, HEPES buffer, citrate buffer, and phosphate buffer.

20. The method according to claim 18, wherein, prior to hydroxyapatite column chromatography step (vi), the filtrate obtained from step (iii)(c) is subjected to ion exchange chromatography.

21. The method according to claim 18, wherein, prior to hydroxyapatite column chromatography step (vi), the filtrate obtained from step (iii)(c) is subjected to anion exchange filtration using a membrane adsorber.

22. The method according to claim 18, wherein the cells containing said hydrophobic protein are host cells selected from the group consisting of *E. coli*, yeasts, plant cells, insect cells, avian cells or mammalian cells.

23. The method according to claim 18, wherein the buffer used in step (iii)(c) contains a detergent selected from the group consisting of anionic detergents, cationic detergents, zwitterionic detergents and non-ionic detergents,
- wherein the anionic detergents are selected from the group consisting of cholic acids and derivatives thereof, N,N-dimethyldodecylamine N-oxide, sodium 1-alkylsulfonates, N lauroylsarcosine or fatty acid salts;

wherein the cationic detergents are selected from the group consisting of alkyl trimethyl ammonium bromide and derivatives thereof or benzalkonium chloride;

wherein the zwitterionic detergents are selected from the group consisting of dodecyl betaine, alkyl dimethylamine oxide and derivatives thereof or 3-(N,N-dimethylalkyl-ammonio)-propanesulfonates; and wherein the non-ionic detergents are selected from the group consisting of octylphenol ethoxylates, polyoxyethylene sorbitan monooleates, alkyl poly(ethylene oxides) and derivatives thereof, alkyl polyglucosides or fatty alcohols.

24. The method of claim 23, wherein the detergent is present in an amount from about 0.5% to about 3.0%.

25. The method of claim 23, wherein the detergent is present in an amount from about 1% to about 1.5%.

26. The method according to claim 17, wherein the buffer used in step (iii)(c) is Tris-buffer.

27. The method according to claim 18, wherein the buffer used in step (iii)(c) contains octylphenol ethoxylate as a detergent.

28. The method according to claim 18, wherein, after step (iii)(c), a microfiltration and/or microdiafiltration step is performed using a 0.2 μm pore size microfiltration cassette.

29. The method according to claim 18, wherein the buffer concentrations are in a range from about 0.1 mM to about 1.0M.

30. The method of claim 18, wherein the buffer concentrations are in a range from about 1.0 mM to about 600 mM.

31. The method of claim 18, wherein the pH of the buffers ranges from about 3.0 to about 10.0.

32. The method of claim 18, wherein the pH of the buffers ranges from about 6.0 to about 8.0.

33. The method of claim 18, wherein the method is carried out at room temperature.

34. The method of claim 18, wherein the method is carried out at a temperature from about 0° C. to about 15° C.

35. The method of claim 1, further comprising a step of ultrafiltration between step (iii) and step (iv).

36. The method of claim 1, further comprising a final step of sterile filtration.

37. The method of claim 36, further comprising a step of ultrafiltration between step (iv) and the final step of sterile filtration.

38. The method of claim 18, further comprising a step of ultrafiltration between step (v) and step (vi).

39. The method of claim 18, further comprising a final step of sterile filtration.

40. The method of claim 39, further comprising a step of ultrafiltration between step (vi) and the final step of sterile filtration.

* * * * *